United States Patent [19]
Urbahns et al.

[11] Patent Number: 6,121,284
[45] Date of Patent: *Sep. 19, 2000

[54] 2,3-BRIDGED 1,4-DIHYDROPYRIDINES, AND THEIR USE AS MEDICAMENTS

[75] Inventors: Klaus Urbahns; Siegfried Goldmann, both of Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor de Vry, Rösrath, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/516,804

[22] Filed: Aug. 18, 1995

[30] Foreign Application Priority Data

Aug. 25, 1994 [DE] Germany .................. 44 30 092

[51] Int. Cl.⁷ .................. A61K 31/47; C07D 215/54
[52] U.S. Cl. .................. 514/311; 514/314; 546/170
[58] Field of Search .................. 546/167, 170; 514/311, 314

[56] References Cited

U.S. PATENT DOCUMENTS

| | | | |
|---|---|---|---|
| 4,021,434 | 5/1977 | Murakami et al. | 424/266 |
| 4,720,572 | 1/1988 | Stubbe | 560/104 |
| 5,328,931 | 7/1994 | Rosen et al. | 546/322 |

FOREIGN PATENT DOCUMENTS

| | | |
|---|---|---|
| 0158138 | 10/1985 | European Pat. Off. . |
| 0209701 | 1/1987 | European Pat. Off. . |
| 0258729 | 3/1988 | European Pat. Off. . |
| 20 03 148 | 7/1971 | Germany . |

OTHER PUBLICATIONS

J.C. Ellory, et al., Br. J. Pharmacol., vol. 111, pp. 903–905, (1994).
J.C. Ellory, et al., Br. J. Pharmacol., vol. 106, pp. 972–977, (1992).
J.C. Ellory, et al., FEBS, vol. 296, No. 2, pp. 219–221, (1992).
U. Rose, Arzneim.–Forsch./Drug Res., vol. 41, No. 3, pp. 199–203, (1991).
P.W.L. Tas, et al., Neuroscience Letters, vol. 94, pp. 279–284, (1988).
Zandersons et. al., J. Chem. Res. Miniprint, vol. 9, p. 2401–2410 (1993)–(Print–out from File Beilstein Search Provided).

*Primary Examiner*—Bernard Dentz
*Attorney, Agent, or Firm*—Sprung Kramer Schaefer & Briscoe

[57] ABSTRACT

The present invention relates to new 2,3-bridged 1,4-dihydropyridines of the general formula (I),

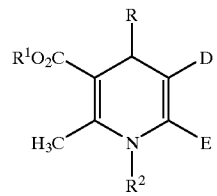

in which R, R¹, R², D and E have the meaning given in the description, processes for their preparation and their use as medicaments, preferably for treatment of the central nervous system.

11 Claims, No Drawings

2,3-BRIDGED 1,4-DIHYDROPYRIDINES, AND THEIR USE AS MEDICAMENTS

The present invention relates to new 2,3-bridged 1,4-dihydropyridines, processes for their preparation and their use as medicaments, preferably for the treatment of the central nervous system.

1,4,5,6,7,8-Hexahydro-5-oxoquinolines and 1,2,3,4,5,6,7,8,9,10-decahydro-1,8-dioxoacridines having a spasmolytic and antihypertensive action are already known from the publication DE 20 031 48.

Moreover, 1-substituted 1,4-dihydropyridine derivatives which have a cerebral circulation-increasing action are known [cf. DE 23 028 66].

The invention relates to new 2,3-bridged 1,4-dihydropyridines of the general formula (I)

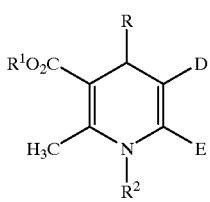

in which
R represents aryl having 6 to 10 carbon atoms or pyridyl, each of which is optionally substituted up to 5-fold in an identical or different manner by cyano, halogen, trifluoromethyl or by straight-chain or branched alkylthio having up to 6 carbon atoms,
$R^1$ represents hydrogen, or represents straight-chain or branched alkyl having up to 8 carbon atoms,
$R^2$ represents straight-chain or branched alkyl having up to 6 carbon atoms, or represents cycloalkyl having 3 to 6 carbon atoms, and
D and E together represent a bivalent radical of the formula $-CO-(CH_2)_3-$, $-CO-CH_2-C(CH_3)_2-CH_2-$, $-CO-O-CH_2-$ or $-CH_2-O-CO-$,
and salts thereof.

Surprisingly, the inventions display a specific and selective, modulating action on potassium channels, and are thus suitable for use as medicaments, in particular as agents for combating diseases of the central nervous system and sickle cell anemia.

Physiologically acceptable salts are in general salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, maleic acid, citric acid, tartaric acid, lactic acid or benzoic acid, or methanesulphonic acid, ethanesulphonic acid, phenylsulphonic acid, toluenesulphonic acid or naphthalenedisulphonic acid.

The compounds according to the invention can exist in stereoisomeric forms which either behave as mirror images (enantiomers) or do not behave as mirror images (diastereomers). The invention relates both to the antipodes and to the racemic forms as well as the diastereomer mixtures. The racemic forms, like the diastereomers, can be separated into the stereoisomerically uniform constituents in a known manner.

Preferred compounds are those of the general formula (I) in which
R represents phenyl, naphthyl or pyridyl, each of which is optionally substituted up to 3-fold in an identical or different manner by cyano, fluorine, chlorine, bromine, iodine, trifluoromethyl or by straight-chain or branched alkylthio having up to 4 carbon atoms,
$R^1$ represents hydrogen, or represents straight-chain or branched alkyl having up to 6 carbon atoms,
$R^2$ represents straight-chain or branched alkyl having up to 4 carbon atoms, cyclopropyl, cyclopentyl or cyclohexyl and
D and E together represent a radical of the formula $-CO-(CH_2)_3-$, $-CO-CH_2-C(CH_3)_2-CH_2-$, $-CO-O-CH_2-$ or $-CO_2-O-CO-$,
and salts thereof.

Particularly preferred compounds of the general formula (I) are those in which
R represents phenyl or pyridyl, each of which is optionally substituted up to 2-fold in an identical or different manner by cyano, fluorine, chlorine, trifluoromethyl or by methylthio,
$R^1$ represents straight-chain or branched alkyl having up to 4 carbon atoms,
$R^2$ represents methyl, ethyl or cyclopropyl and
D and E together represent a radical of the formula $-CO-(CH_2)_3-$, $-CO-CH_2-C(CH_3)_2-CH_2-$, $-CO-O-CH_2-$ or $-CH_2-O-CO-$,
and salts thereof The compounds of the general formula (I) according to the invention display an unforeseeable, valuable pharmacological action spectrum.

They are channel modulators having a surprising selectivity for large conductance for calcium-dependent potassium channels (BK(Ca) channels), in particular potassium channel modulators of the central nervous system. At the same time, they are distinguished by the absence of significant calcium-antagonistic and calcium-agonistic actions.

On the basis of pharmacological properties, they can be employed for the preparation of medicaments for the treatment of centrally degenerative diseases, such as, for example, with the occurrence of dementias (multi-infarction dementia (MID), primary degenerative dementia (PDD), presenile and senile Alzheimer's disease, HIV dementia and other forms of dementia), Parkinson's disease or amyotrophic lateral sclerosis, as well as multiple sclerosis.

The active compounds are also suitable for the treatment of age-related disturbances in cerebral performance, organic brain syndrome (OBS) and age-associated memory impairment (AAMI).

They are suitable for prophylaxis and treatment and for combating the consequences of cerebral circulatory disturbances, such as cerebral ischaemias, apoplexies and craneocerebral traumas and of subarachnoid haemorrhages.

They are valuable for the treatment of depressions and psychoses, for example schizophrenia. They are furthermore suitable for the treatment of disturbances in neuroendocrine secretion and in neurotransmitter secretion and associated disturbances in health, such as mania, alcoholism, drug abuse, addiction or pathological eating behaviour. Other fields of use are the treatment of migraine, sleep disturbances and neuropathy. They are moreover suitable as analgesics.

The active compounds furthermore are suitable for treatment of disturbances of the immune system, in particular T-lymphocyte proliferation, and for influencing the smooth musculature, in particular of the uterus, urinary bladder and bronchial tract, and for the treatment of associated diseases, such as, for example, asthma and urinary incontinence, and for the treatment of arrhythmia, angina and diabetes.

The compounds of the general formula (I) according to the invention can be prepared by a process in which

[A] in the case D/E ≠—CH$_2$—O—CO— aldehydes of the general formula (II)

R—CHO (II)

in which

R comprises the abovementioned scope of meaning, are first converted, by reaction with the compounds of the general formulae (III) and (IV)

(III)

(IV)

in which

R$^1$, D and E have the abovermentioned meaning, but R$^1$ does not represent hydrogen, in inert solvents and if appropriate in the presence of a base and/or auxiliary, into the compounds of the general formula (V)

(V)

in which

R, R$^1$, D and E have the aforementioned meaning, and the products are then reacted with alkylating agents of the formula (VI)

R$^2$—X (VI)

in which

R$^2$ has the above mentioned meaning and

X represents halogen, preferably iodine, by customary methods, or

[B] in the case where D/E represent the radical of the formula —CH$_2$—O—CO, 2-amino-2-buten4-olide of the formula (VII)

(VII)

is reacted with benylidene compounds of the general formula (VIII)

(VIII)

in which

R and R$^1$ have the above mentioned meaning, in inert solvents in the presence of acetic acid to give compounds of the general formula (IX)

(IX)

in which

R and R$^1$ have the above mentioned meaning, and an alkylation is then carried out by means of customary agents, and in the case where R$^1$=H, the esters are hydrolysed by customary methods.

The process according to the invention can be illustrated by way of example by the following equations:

[A]

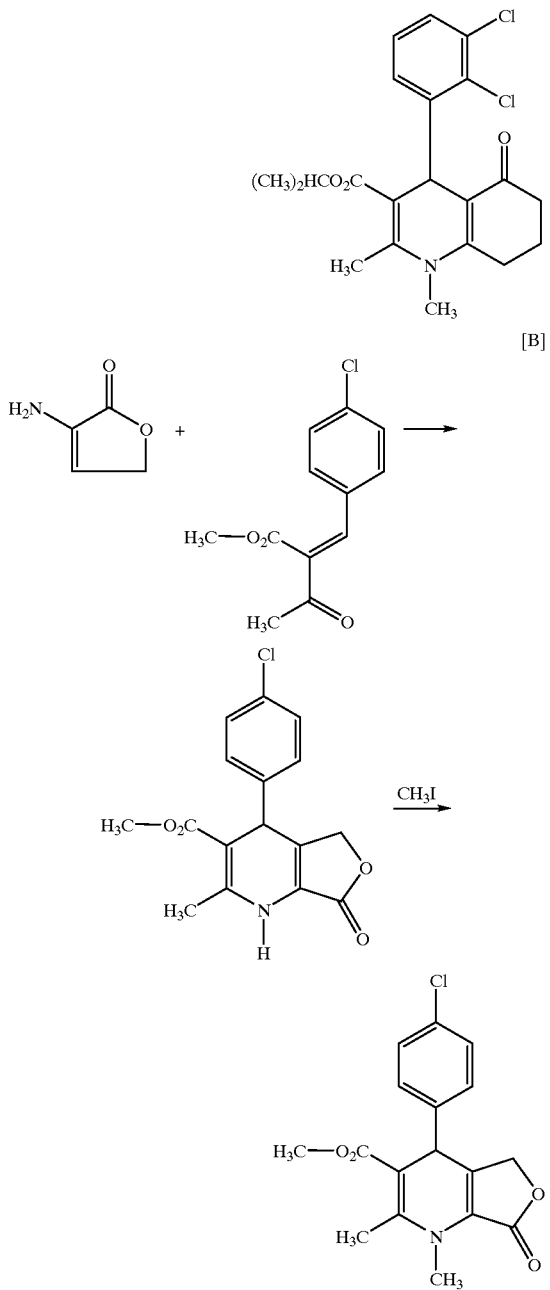

Suitable solvents for his reaction are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, acetonitrile, acetone or amides, such as hexamethylphosphoric acid triamide or dimethylformamide, or halogenated hydrocarbons, such as methylene chloride or carbon tetrachloride, or hydrocarbons, such as benzene or toluene. It is also possible to use mixtures of the solvents mentioned. Isopropanol, ethanol, tetrahydrofuran, methanol, dioxane, acetone and dimethylformamide are particularly preferred.

Suitable bases are in general alkali metal hydrides, carbonates or alcoholates, such as, for example, sodium hydride, potassium carbonate or potassium tert-butylate, or cyclic amines, such as, for example, piperidine or dimethylaminopyridine, or $C_1$–$C_4$-alkylamines, such as, for example, triethylamine. Piperidine, dimethylaminopyridine, pyridine, sodium hydride, potassium tert-butylate and potassium carbonate are preferred, depending on the particular reaction steps.

Any desired ratio of the substances participating in the reaction can be used for carrying out the process according to the invention. In general, however, molar amounts of the reactants are used.

The reaction temperatures can be varied within a relatively wide range. In general, the reaction is carried out at between +10° C. and +150° C., preferably between +20° C. and +100° C., in particular at the boiling point of the particular solvent.

The reactions can be carried out under normal pressure, but also under increased or reduced pressure (for example 0.5 to 3 bar). They are in general carried out under normal pressure.

Suitable solvents for the alkylation are likewise customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned. Dimethylformamide is preferred.

Suitable bases are in general alkali metal hydrides or alcoholates, such as, for example, sodium hydride or potassium tert-butylate, or cyclic amines, such as, for example, piperidine or dimethylaminopyrdine, or $C_1$–$C_4$-alkylamines, such as, for example, triethylamine. Sodium hydride is preferred.

The reaction temperatures can be varied within a relatively wide range. In general, the reaction is carried out at between –10° C. and 150° C., preferably between +20° C. and +100° C., in particular at room temperature.

The alkylation is carried out in the above mentioned solvents at tempts of –5° C. to +150° C., preferably at 0° C. to +100° C.

The reactions can be carried out under normal pressure, but also under increased or reduced pressure (for example 0.5 to 3 bar). They are in general carried out under normal pressure.

The base is in general employed in an amount of from 1 mol to 3 mol, preferably 1 mol to 2 mol, in each case per mol of the compounds to be alkylated.

Enantiomerically pure forms are obtained, for example, by a process in which diastereomer mixtues of the compounds of the general formula (I) in which $R^1/R^{1'}$ represents an optically active ester radical are separated by customary methods and are then either esterified directly, or the chiral carboxylic acids are first prepared and then the enantiomerically pure dihydropyridines are prepared by esterification.

The diastereomers are in general separated either by fractional crystallization, by column chromatography or by Craig partition. The optimum process must be decided from case to case, and sometimes it is also expedient to use combinations of the individual processes. Separation by crystallization or Craig partition or a combination of the two processes is particularly suitable.

The enantiomerically pure compounds are also accessible by chromatography of the racemic esters on chiral phases.

The compounds of the general formulae (II), (III), (IV), (V), (VI), (VII) and (VIII) are known or can be prepared by customary methods.

The new compounds of the general formula (I) according to the invention display a valuable, unforeseeable action spectrum, in particular on the basis of their selectivity for large conductance for calcium-dependent potassium channels of high conductivity.

$^{86}$Rubidium Efflux from C6-BU1-glioma cells

The experiments were carried out in accordance with the method described by Tas et al. (Neurosci. Lett. 94, 279–284, (1988)), with slight changes. The increase in efflux above the basal efflux caused by ionomycin is calculated from the data and set at 100%. The stimulations in the presence of test substances are then based on this value.

Test Data

EXAMPLE 1

Isopropyl 4-(2,3-dichlorophenyl)-1,2-dimethyl-5-oxo-1,4,5,7,8-hexahydroquinoline-3-carboxylate 38% residual efflux with 1 μM test substance applied.

EXAMPLE 8

Methyl 1,4,5,7-tetrahydro-4-(4-chlorophenyl)-1,2-dimethyl-7-oxo-furo-[3,4b]-pyridine-3-carboxylate 53% residual efflux with 1 μM test substance applied.

EXAMPLE 11

Methyl 1,4,5,7-tetrahydro-4-(2,3-difluorophenyl)-1,2-dimethyl-5-oxo-furo-[3,4b]-pyridine-3-carboxylate 73% residual efflux with 1 μM test substance applied.

The present invention also relates to pharmaceutical formulations which comprise, in addition to inert, non-toxic, pharmaceutically suitable auxiliaries and excipients, one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

In addition to the active compounds of the formula (I), the pharmaceutical formulations can also comprise other pharmaceutical active compounds.

The above mentioned pharmaceutical formulations can be prepared by known methods in the customary manner, for example using the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of bodyweight every 24 hours, if appropriate in the form of several individual doses, in order to achieve the desired result.

However, where appropriate, it may be advantageous to deviate from the amounts mentioned, and in particular as a function of the nature and bodyweight of the subject treated, of the behaviour of the individual towards the medicament, of the nature and severity of the disease, of the nature of the formulation and administration, and of the time or interval at which administration takes place.

Mobile Phase Mixtures
a: Methylene chloride/AcOEt 10+1
b: Methylene chloride/MeOH 10+1
c: PE/AcOEt 7+3

Starting Compounds

Example I

Methyl 1,4,5,7-tetrahydro-4-(4-chlorophenyl)-2-methyl-5-oxo-furo-(3,4b)-pyridine-3-carboxylate

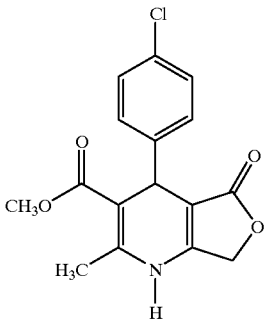

3 g (21.3 mmol) of 4-chlorobenzaldehyde, 4.0 g (21.3 mmol) of methyl 4-acetoxyacetoacetate (preparation according to DE 84 34436 78) and 2.5 g (21.3 mmol) of methyl 3-aminocrotonate are dissolved in 40 ml of isopropanol and the solution is heated under reflux for 12 hours. 10 ml of dilute aqueous HCl are then added and the mixture is heated under reflux for a further 30 minutes. The mixture is partitioned between toluene and water. Drying (MgSO$_4$) and concentration of the organic phase gives a white solid, which is purified by filtration over 50 g of silica gel (AcOEt:PE 1+1) and subsequent recrystallization from AcOEt/PE. 2.6 g (8.13 mmol, 38% of theory) of the title compound are obtained.

Example II

Isopropyl 4-(2,3-dichlorophenyl)2-methyl-5-oxo-1,4,5,7,8-hexahydroquinoline-3-carboxylate

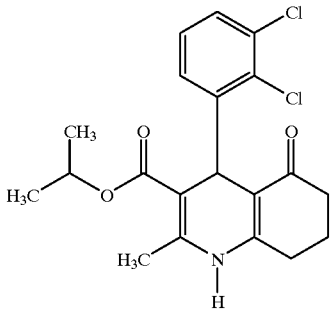

3.50 g (20 mmol) of 2,3-dichlorobenzaldehyde, 2.24 g (20 mmol) of dihydroresorcinol and 2.86 g (20 mmol) of isopropyl 3-aminocrotonate are dissolved in 100 ml of isopropanol and the solution is stirred under reflux for 5 hours. The product precipitates. 50 ml of water are added and the mixture is cooled to room B The product is filtered off with suction and washed successively with isopropanol, ethanol and ether.

Yield: 5.8 g (74% of theory)

Example III

2-Azido-γ-butyrolactone

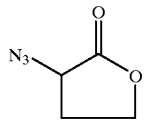

1.56 g (10 mmol) of 2-bromo-,γ-butyrolactone are dissolved in 2 ml of dimethylformamide, and 612 mg (12.5 mmol) of lithium azide are added at 0° C. The mixture is stirred at room temperature for 2 hours, water is added and the mixture is extracted three times with methylene chloride. The combined organic phases are washed three times with water, dried over sodium sulphate and concentrated. 1.10 g (86.6% of theory) of the title compound are obtained.

MS: 127

Example IV

2-Amino-buten-4-olide

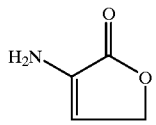

1.02 g (0.8 mmol) of the compound from Example III in 2 ml of ethanol are added dropwise to a solution of 50 g of sodium in 5 ml of ethanol at 20° C. The mixture is stirred at room temperature for 30 minutes and concentrated under reduced pressure. The solid which has precipitated out is extracted by stirring in ethanol, and the residue is dissolved in hot ethyl acetate. The solution is filtered and concentrated. 350 mg (44% of theory) of colourless solid are obtained.

MS: 99

Example V

Isopropyl ,4,5,7-tetrahydro-4-(2,3-dichlorophenyl)-2-methyl-7-oxo-furo[3,4-b]pyridine-3-carboxylate

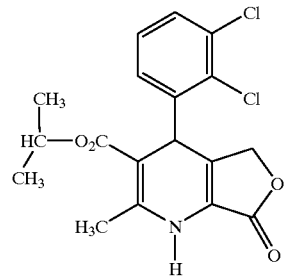

9.0 g (30 mmol) of isopropyl 2-acetyl-3-(2,3-dichlorophenyl)acrylate and 3.0 g (30 mmol) of the compound from Example IV are dissolved in 60 ml of isopropanol, and 1.7 ml (30 mmol) of AcOH are added. The mixture is kept under reflux for 20 hours. It is then concentrated and the residue is purified by chormatography over 100 g of silica gel 60 (ethyl acetate/petroleum ether 10:1, then 5:1). The resulting material is recrystallized from ether.

4.08 g (36% of theory) of the title compound are obtained. MS: 381, Rf=0.61 (petroleum ether/AcOEt=7+3)

Preparation Examples

Example 1

Isopropyl 4-(2,3-dichlorophenyl)-1,2-dimethyl-5-oxo-1,4,5,7,8-hexahydroquinoline-3-carboxylate

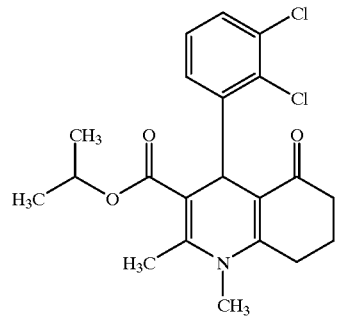

1.5 g (3.8 mmol) of isopropyl 4-2,3dichlorophenyl-2-methyl-5-oxo-1,4,5,7,8-hexahydroquinoline-3-carboxylate are dissolved in 20 ml of dimethylformamide, and 138 mg (4.6 mmol) of NaH are added at 0° C. The mixture is stirred at room temperature for 15 minutes, 1.08 g (7.6 mmol) of methyl iodide are added at 0° C. and the mixture is stirred again at room tempera for 30 minutes. Water is added and the mixture is extracted 3 times with AcOEt. The organic phase is washed 5 times with water, dried and concentrated. The residue is recrystallized from isopropanol/petroleum ether.

1.20 g (77% of theory) are obtained. MS: 407, Rf=0.52 (a)

The compounds shown in Table 1 are prepared analogously to the instructions of Example 1:

TABLE 1

| Example No. | X, Y | $R^1$ | Yield (% of theory) | Melting point (° C.)/ $R_f$/MS |
|---|---|---|---|---|
| 2 | 3-H, 4-Cl | $CH_3$ | 72 | 0.42 ($CH_2Cl_2$/AcOEt 10 + 1) 345 |
| 3 | 2-Cl, 3-Cl | —$CH_3$ | 74 | 0.33 ($CH_2Cl_2$/AcOEt 10 + 1) 379 |

Example 4

Isopropyl 4-(2,3-dichlorophenyl)-1,2,7,7-tetramethyl-5-oxo-1,4,5,6,7,8-hexahydroquinoline-3-carboxylate

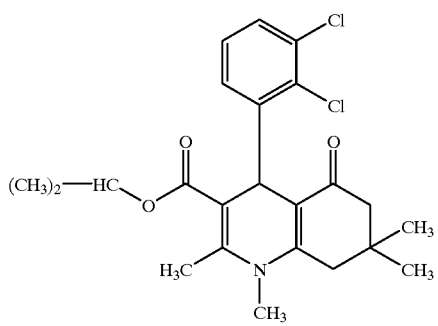

Analogously to instructions for Example 1, 0.98 g (63% of theory) of the title compound are obtained from 1.5 g (3.55 mol) of isopropyl 4-2,3dichlorophenyl)-2-methyl-5-oxo-1,4,5,6,7,8-hexahydroquinoline-3-carboxylate by methylation of 1.04 g (7.14 mol) of methyl iodide in dimethylformamide.

Yield: 60% of theory

Rf=0.59 (CH$_2$Cl$_2$/AcOEt=10+1), MS: 435

The compounds shown in Table 2 are prepared analogously to the instructions of Example 4:

TABLE 2

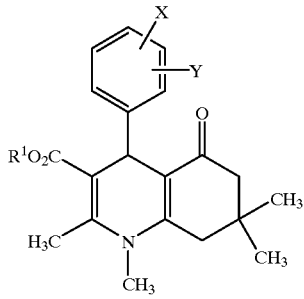

| Example No. | X, Y | R$^1$ | Yield (% of theory) | Melting point (° C.)/R$_f$ |
|---|---|---|---|---|
| 5 | 3-H, 4-Cl | CH$_3$ | 76 | 0.9 (CH$_2$Cl$_2$/MeOH 10 + 1) |
| 6 | 2-Cl, 4-Cl | CH$_3$ | 77 | 0.85 (CH$_2$Cl$_2$/MeOH 10 + 1) |

Example 7

Isopropyl 1,4,5,7-tetrahydro-4-(3,4-dichlorophenyl)-1,2-dimethyl-5-oxo-furo[3,4-b]-pyridine-3-carboxylate

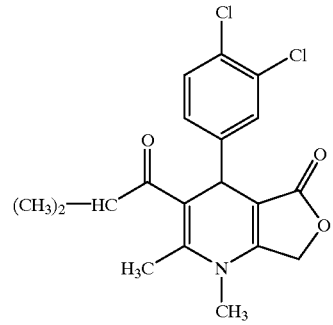

Analogously to the instructions for Example 1, 1.07 g of the title compound are obtained from 2.0 g (5.24 mol) of methyl 1,4,5,7-tetrahydro-4-(4-chlorophenyl)-2-methyl-5-oxo-furo[3,4-b]pyridine-3-carboxylate by methylation with 1.47 g (10.4 mol) of methyl iodide in dimethylformamide.

Yield: 29% of theory

R$_f$=0.40 (CH$_2$Cl$_2$/AcOEt 10+1), MS: 395

The compounds shown in Table 3 are prepared analogously to the instructions of Example 7:

TABLE 3

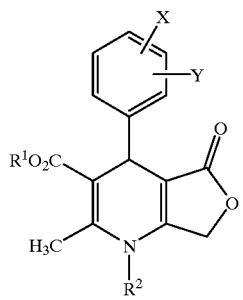

| Example No. | X, Y | R$^1$ | R$^2$ | Yield (% of theory) | Melting point (° C.)/R$_f$ |
|---|---|---|---|---|---|
| 8 | 3-Cl, 3-H | CH$_3$ | CH$_3$ | 54 | 167–70 |
| 9 | 2-Cl, 3-Cl | (CH$_3$)$_2$HC— | C$_2$H$_5$ | 9 | 154–55 |
| 10 | 2-Cl, 3-Cl | CH$_3$ | CH$_3$ | 69 | 0.72/b |
| 11 | 2-F, 3-F | CH$_3$ | CH$_3$ | 65 | 0.29/a |
| 12 | 4-F | CH$_3$ | CH$_3$ | 35 | 0.28/a |
| 13 | 2-F, 6-Cl | CH$_3$ | CH$_3$ | 34 | 0.37/a |

Example 14

Isopropyl 1,4,5,7-tetrahydroo4-(2,3-dichlorophenyl)-1,2dimethyl-7-oxo-furo[3,4-b]-pyridine-3-carboxylate

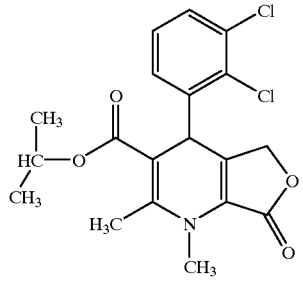

1.5 g (3.92 mmol) of isopropyl 1,4,5,7-tetrahydro-4(2,3-dichlorophenyl)2-methyl-7-oxo-furo[3,4-b]pyridine-3 carboxylate are reacted with 141 mg (4.70 mmol) of NaH and 1.11 g (7.84 mml) of methyl iodide to give 0.97 g (63% of theory).

MS: 395

$R_f$=0.61 (PE/AcOEt =7+3)

The compounds shown in Table 4 are prepared analogously to the instructions of Example 14:

TABLE 4

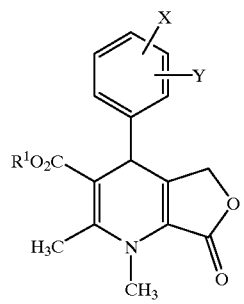

| Example No. | $R^1$ | $R^2$ | Yield (% of theory) | Rf* |
|---|---|---|---|---|
| 15 | —CH(CH$_3$)$_2$ | 2-Cl, 3-Cl | 63 | 0.61/c |
| 16 | —CH(CH$_3$)$_2$ | 4-Cl | 47 | 0.65/c |
| 17 | —CH$_3$ | 2-Cl, 3-Cl | 62 | 0.47/c |

We claim:

1. A 2,3-bridged 1,4-dihydropyridine compound selected from the group consisting of:
   a) Isopropyl 4-(2,3-dichlorophenyl)-1,2-dimethyl-5-oxo-1,4,5,6,7,8-hexahydroquinoline-3-carboxylate;
   b) Methyl 4-(4-chlorophenyl)-1,2-dimethyl-5-oxo-1,4,5,6,7,8-hexahydroquinoline-3-carboxylate; and
   c) Methyl 4-(2,3-dichlorophenyl)-1,2-dimethyl-5-oxo-1,4,5,6,7,8-hexahydroquinoline-3-carboxylate.

2. A pharmaceutical composition comprising a 2,3-bridged 1,4-dihydropyridine compound according to claim 1 and a pharmaceutically acceptable auxiliary or excipient.

3. A method of treating sickle cell anemia in a patient suffering therefrom comprising administering to said patient an effective amount therefor of a 2,3-bridged 1,4-dihydropyridine of the formula:

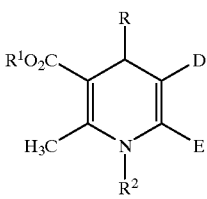

(I)

wherein
R represents aryl having 6 to 10 carbon atoms or pyridyl, each of which is optionally substituted by 1 to 5 identical or different substituents independently selected from the group consisting of cyano, halogen, trifluoromethyl and straight-chain and branched alkylthio having 1 to 6 carbon atoms;

$R^1$ represents hydrogen or straight-chain or branched alkyl having 1 to 8 carbon atoms;

$R^2$ represents straight-chain or branched alkyl having 1 to 6 carbon atoms or cycloalkyl having 3 to 6 carbon atoms; and D and E together represent —CO—(CH$_2$)$_3$— or —CO—CH$_2$—C(CH$_3$)$_2$—CH$_2$—.

4. The method according to claim 3, wherein in formula (I) therein:

R represents phenyl, naphthyl or pyridyl, each of which is optionally substituted by 1 to 3 identical or different substituents independently selected from the group consisting of cyano, fluorine, chlorine, bromine, iodine, trifluoromethyl and straight-chain and branched alkylthio having 1 to 4 carbon atoms;

$R^1$ represents hydrogen or straight-chain or branched alkyl having 1 to 6 carbon atoms;

$R^2$ represents straight-chain or branched alkyl having 1 to 4 carbon atoms or cyclopropyl, cyclopentyl or cyclohexyl.

5. The method according to claim 3, wherein in formula (I) therein:

R represents phenyl or pyridyl, each of which is optionally substituted by 1 to 2 identical or different substituents independently selected from the group consisting of cyano, fluorine, chlorine, trifluoromethyl and methylthio;

$R^1$ represents straight-chain or branched alkyl having 1 to 4 carbon atoms;

$R^2$ represents methyl, ethyl or cyclopropyl.

6. A method of treating depression in a patient suffering therefrom comprising administering to said patient an effective amount therefor of a 2,3-bridged 1,4-dihydropyridine of the formula:

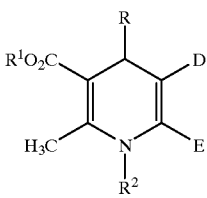

(I)

wherein
R represents aryl having 6 to 10 carbon atoms or pyridyl, each of which is optionally substituted by 1 to 5 identical or different substituents independently selected from the group consisting of cyano, halogen, trifluoromethyl and straight-chain and branched alkylthio having 1 to 6 carbon atoms;

$R^1$ represents hydrogen or straight-chain or branched alkyl having 1 to 8 carbon atoms;

$R^2$ represents straight-chain or branched alkyl having 1 to 6 carbon atoms or cycloalkyl having 3 to 6 carbon atoms; and D and E together represent —CO—$(CH_2)_3$— or —CO—$CH_2$—$C(CH_3)_2$—$CH_2$—.

7. The method according to claim 6, wherein in formula (I) therein:

R represents phenyl, naphthyl or pyridyl, each of which is optionally substituted by 1 to 3 identical or different substituents independently selected from the group consisting of cyano, fluorine, chlorine, bromine, iodine, trifluoromethyl and straight-chain and branched alkylthio having 1 to 4 carbon atoms;

$R^1$ represents hydrogen or straight-chain or branched alkyl having 1 to 6 carbon atoms;

$R^2$ represents straight-chain or branched alkyl having 1 to 4 carbon atoms or cyclopropyl, cyclopentyl or cyclohexyl.

8. The method according to claim 6, wherein in formula (I) therein:

R represents phenyl or pyridyl, each of which is optionally substituted by 1 to 2 identical or different substituents independently selected from the group consisting of cyano, fluorine, chlorine, trifluoromethyl and methylthio;

$R^1$ represents straight-chain or branched alkyl having 1 to 4 carbon atoms;

$R^2$ represents methyl, ethyl or cyclopropyl.

9. A method of treating psychoses in a patient suffering therefrom comprising administering to said patient an effective amount therefor of a 2,3-bridged 1,4-dihydropyridine of the formula:

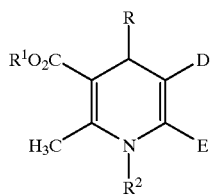

(I)

wherein

R represents aryl having 6 to 10 carbon atoms or pyridyl, each of which is optionally substituted by 1 to 5 identical or different substituents independently selected from the group consisting of cyano, halogen, trifluoromethyl and straight-chain and branched alkylthio having 1 to 6 carbon atoms;

$R^1$ represents hydrogen or straight-chain or branched alkyl having 1 to 8 carbon atoms;

$R^2$ represents straight-chain or branched alkyl having 1 to 6 carbon atoms or cycloalkyl having 3 to 6 carbon atoms; and D and E together represent —CO—$(CH_2)_3$— or —CO—$CH_2$—$C(CH_3)_2$—$CH_2$—.

10. The method according to claim 9, wherein in formula (I) therein:

R represents phenyl, naphthyl or pyridyl, each of which is optionally substituted by 1 to 3 identical or different substituents independently selected from the group consisting of cyano, fluorine, chlorine, bromine, iodine, trifluoromethyl and straight-chain and branched alkylthio having 1 to 4 carbon atoms;

$R^1$ represents hydrogen or straight-chain or branched alkyl having 1 to 6 carbon atoms;

$R^2$ represents straight-chain or branched alkyl having 1 to 4 carbon atoms or cyclopropyl, cyclopentyl or cyclohexyl.

11. The method according to claim 9, wherein in formula (I) therein:

R represents phenyl or pyridyl, each of which is optionally substituted by 1 to 2 identical or different substituents independently selected from the group consisting of cyano, fluorine, chlorine, trifluoromethyl and methylthio;

$R^1$ represents straight-chain or branched alkyl having 1 to 4 carbon atoms;

$R^2$ represents methyl, ethyl or cyclopropyl.

* * * * *